United States Patent
Grieshober, Jr. et al.

(10) Patent No.: US 10,098,340 B2
(45) Date of Patent: Oct. 16, 2018

(54) METHOD FOR PRESERVING CELLS AND CELL CULTURES

(75) Inventors: William E. Grieshober, Jr., East Amherst, NY (US); James S. Jones, Newton, MA (US); Semyon Kogan, Newton, MA (US); Ilya Ilyin, St. Petersburg (RU); Natella I. Enukashvily, St. Petersburg (RU); Yana A. Filkina, St. Petersburg (RU); Alexander N. Shumeev, St. Petersburg (RU); Stanislav Kolchanov, St. Petersburg (RU)

(73) Assignee: Rich Technologies Holding Company, LLC, Buffalo, NY (US)

( * ) Notice: Subject to any disclaimer, the term of this patent is extended or adjusted under 35 U.S.C. 154(b) by 874 days.

(21) Appl. No.: 13/982,766

(22) PCT Filed: Feb. 3, 2012

(86) PCT No.: PCT/US2012/023790
§ 371 (c)(1),
(2), (4) Date: Sep. 10, 2013

(87) PCT Pub. No.: WO2012/109107
PCT Pub. Date: Aug. 16, 2012

(65) Prior Publication Data
US 2013/0344596 A1     Dec. 26, 2013

Related U.S. Application Data

(60) Provisional application No. 61/436,441, filed on Feb. 7, 2011.

(51) Int. Cl.
*A01N 1/02*     (2006.01)
(52) U.S. Cl.
CPC .......... *A01N 1/0284* (2013.01); *A01N 1/0289* (2013.01)
(58) Field of Classification Search
CPC ............................ A01N 1/0284; A01N 1/0289
See application file for complete search history.

(56) References Cited

U.S. PATENT DOCUMENTS

| | | | |
|---|---|---|---|
| 8,158,339 B2 * | 4/2012 | Ilyin | A01N 1/021 424/93.72 |
| 2007/0110821 A1 | 5/2007 | Petzelt et al. | |
| 2008/0031971 A1 | 2/2008 | Petzelt et al. | |
| 2009/0081785 A1 | 3/2009 | Ho et al. | |
| 2009/0311340 A1 | 12/2009 | Franks et al. | |
| 2010/0009334 A1 | 4/2010 | Ilyin et al. | |
| 2010/0196996 A1 | 8/2010 | Kilic et al. | |

OTHER PUBLICATIONS

Spaggiari et al., Antiapoptotic activity of argon and xenon, Cell Cycle, 2013, vol. 12, pp. 2636-2642.*
Boswell et al. "Platelet-Rich Plasma: A Milieu of Bioactive Factors" (2012) Arthroscopy: The Journal of Arthroscopic and Related Surgery, vol. 28, No. 3: 429-439.*
U.S. International Search Authority, International Search Report and Written Opinion dated Apr. 5, 2010 for PCT/US2012/023790.
Cookson et al., Transfusion Medicine, 20(6):392-402 (2010).
Valavanis et al., Method in Cell Biology, 66:417-436 (2001).
Shapiro et al., Diabetes Technologies & Therapeutics, 2(3):449-452 (2000).
De Boer et al., Journal of Hematotherapy & Stem Cells Research, 11(6):951-963 (2004).
Karas et al., Molecular Biology of the Cell, 10:4441-4450 (1999).
Pimental-Muinos et al., Immunity, 11:783-798 (1999).

* cited by examiner

*Primary Examiner* — Teresa E Knight
(74) *Attorney, Agent, or Firm* — Fay Sharpe LLP

(57) ABSTRACT

Provided is a method for reducing apoptosis in nucleated cells. The method entails holding nucleated cells in a container and adding a gas containing xenon to the container so that the pressure inside the container reaches between 0.5 to 4.0 Atm above ambient pressure; holding the container at between 0.5 to 4.0 Atm above ambient pressure for a period of time during which the temperature in the container is between 22° C. and 37° C.; lowering the temperature in the container to between 0.1° C. and 10° C. while maintaining the pressure of 0.5 to 4.0 Atm above ambient pressure and holding the container for a period of time; and reducing the pressure in the container to ambient pressure and increasing the temperature to 22° C.-37° C. By performing these steps, the cells undergo less apoptosis than a reference.

17 Claims, 6 Drawing Sheets

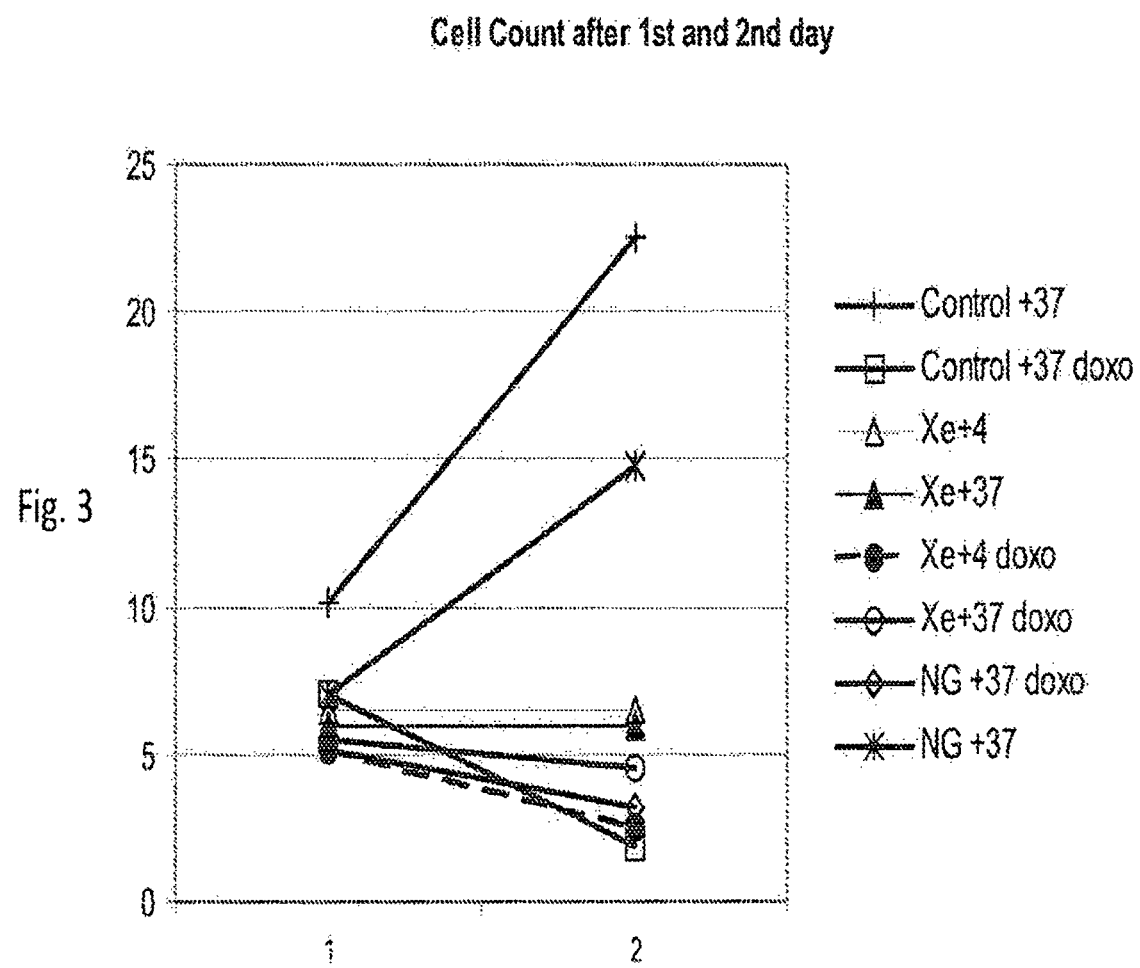

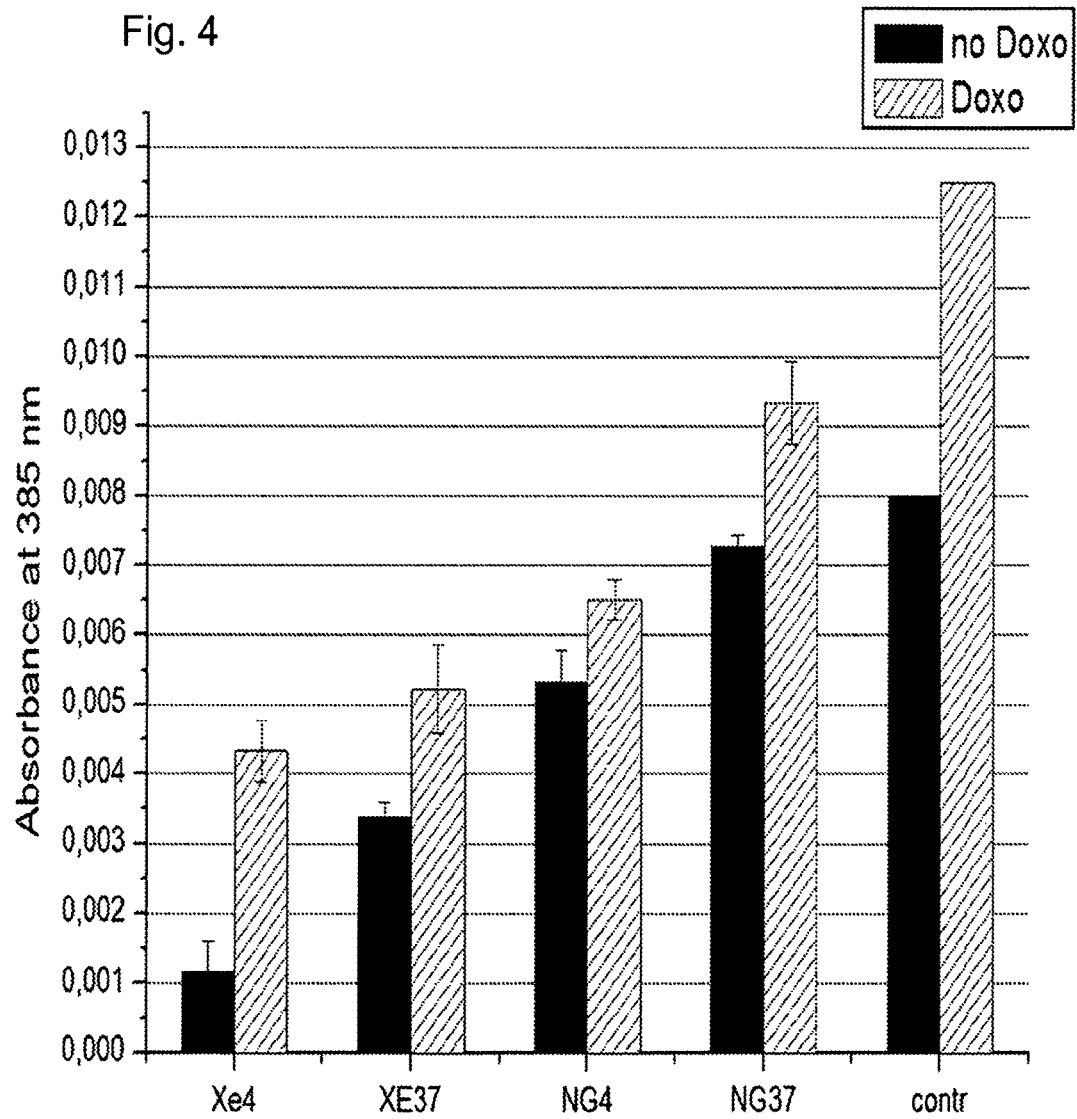

METHOD FOR PRESERVING CELLS AND CELL CULTURES

CROSS-REFERENCE TO RELATED APPLICATION

This application claims priority to U.S. application Ser. No. 61/436,441, filed Feb. 7, 2011, the disclosure of which is incorporated herein by reference.

FIELD OF THE INVENTION

The present invention relates generally to preservation of cells and more particularly to preservation of eukaryotic, nucleated cells in vitro.

BACKGROUND OF THE INVENTION

Storage of biological material comprising living cells during both short and prolonged periods of time represents one of the most significant challenges in modern medical science. Cooling to a temperature within the range −20° C. to −176° C. in the presence of cryoprotecting substances still represents the most broadly used method for storage of living cells. The mechanism of cryo-protection involves preventing formation of ice crystals that destroy cells and/or cellular components. However, these and other conventional methods for cell preservation induce stress on the cells being stored, and apoptosis is almost always induced in a portion of cells that are subjected to manipulations involved in storage. (See, for examples, de Boer F, et al. J Hematother Stem Cell Res. 2002 December; 11 (6):951-63; Shapiro A M, et al. Diabetes Technol Ther. 2000 Autumn; 2 (3):449-52; Cookson P, et al. Transfus Med. 2010 December; 20 (6): 392-402). Further, cells that are obtained directly from organs and tissues and are not cultured are often injured during storage and transportation. Thus, there is an ongoing and unmet need for improved methods for preserving cells and protecting them from lethal events, such as apoptosis, during storage and/or transportation. The present invention meets this and other needs.

SUMMARY OF THE INVENTION

The present invention provides a method for reducing apoptosis. The method comprises the general steps of: i) holding nucleated cells in a container and adding a gas comprising xenon to the container so that the pressure inside the container reaches 0.5 to 4.0 Atm above ambient pressure; ii) holding the container of i) at 0.5 to 4.0 Atm above ambient pressure for a period of time during which the temperature in the container is 22° C.-37° C.; iii) lowering the temperature in the container to 0.1° C.-10° C. while maintaining the pressure of 0.5 to 4.0 Atm above ambient pressure; iv) holding the container at 0.1° C.-10° C. and a pressure of 0.5 to 4.0 Atm above ambient pressure for a period of time; and v) sequentially reducing the pressure in the container of to ambient pressure and increasing the temperature to 22° C.-37° C. Cells treated according to this process undergo less apoptosis than a reference.

In various embodiments, the period of time of during which the container is held at 0.5 to 4.0 Atm above ambient pressure at 22° C.-37° C. is from 15 minutes to 24 hours. The period of time during which the container is held at 0.1° C.-10° C. and a pressure of 0.5 to 4.0 Atm above ambient pressure is from 2 hours to three weeks, which includes but is not necessarily limited to between 2 hours and 24 hours, or at least 2 days, 3 days, 4 days, 5 days, 6 days, 7 days, 8 days, 9 days, 10 days, 11 days, 12 days, 13 days, 14 days, etc., up to three weeks. The method includes reducing apoptosis in mammalian cells, which can be human cells.

The invention also provides a refrigerated composition comprising nucleated cells, wherein the cells are present in a container and are held at a temperature of between 0.1° C. and 10° C., and wherein the pressure inside the container is between 0.5 to 4.0 Atm above ambient pressure due to introducing a gas comprising xenon into the container.

BRIEF DESCRIPTION OF THE DRAWINGS

FIG. 3. shows the change in the numbers of live Jurkat cells in culture after transferring them from storage conditions and placing them under standard cultivation conditions (37° C. in air with 5% CO2). The cells were stained with trypan blue dye before and after 24 hrs incubation under standard condition to determine the cell count. The cells of the control group were grown in standard cultivation conditions at ambient pressure, including the storage period. Control cells were taken at day zero of the experiment from the same flask as the experimental cells and plated on the Petri dishes.

FIG. 4. shows that 4 Atm of excessive pressure obtained by introducing a gas comprising xenon into the container prevented development of both spontaneous (series no Doxo in the diagram) and induced (series Doxo in the diagram) apoptosis in the Jurkat cells. The activity of caspase 3 after 24 hrs of storage was monitored in this set of experiments.

DETAILED DESCRIPTION OF THE INVENTION

Figure 1A:
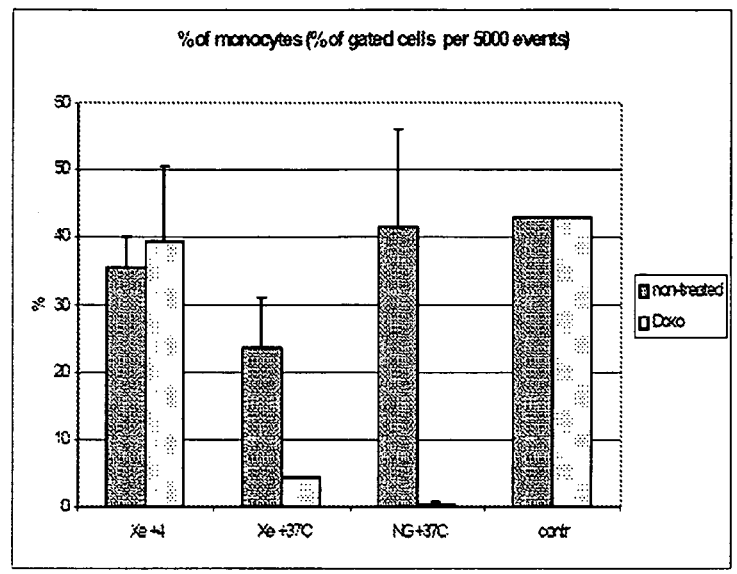
FIG. 1 shows percentage of human leukemic monocyte lymphoma cell line U-937 cells based as determined by flow cytometry after 24 hrs (FIG. 1A) and 7 days (FIG. 1B) of storage at pressure of 4 Atm at the indicated temperatures. Cells were stored in Petri dishes for the indicated period either in a container or in standard CO2 incubator at 37 C designed for cell cultivation ("control"). After removal from storage, the cells were decompressed gradually over a period of 60 minutes, stained with antiCD14 antibody and sorted by flow cytometry. The antiCD14 antibody is a marker of monocytes and macrophages. The percent of total cells that stain positive for antiCD14 antibody are plotted.

The present invention provides methods for inhibiting apoptosis. The method is based on our discovery that treatment of nucleated cells contained in an atmosphere comprising xenon under certain pressures and temperatures as further described herein results in reduced apoptosis in the cells. The invention is particularly suited for reducing apoptosis in cells during storage and/or transportation. In various embodiments, cells treated using the method of the invention can be stored under pressure at a temperature from 0.1° C. to +10° C. for a period of up to two weeks. The invention can be practiced without the use of conventional cryoprotectant agents.

In general, the invention comprises the following sequential steps: i) holding nucleated cells in a container and adding xenon or a gas mixture containing Xe to the container so that the pressure inside the container reaches 0.5 to 4.0 Atm above ambient pressure (1.5 to 5.0 Atm absolute pressure); ii) holding the container of i) at the pressure of 0.5-4 Atm above ambient pressure for a period of time during which the temperature in the container is between 22° C. and 37° C.; iii) lowering the temperature in the container to between 0.1° C.-10° C. while maintaining the pressure of 0.5-4.0 Atm above ambient pressure; iv) holding the container at a temperature of 0.1° C.-10° C. and a pressure of 0.5-4.0 Atm above ambient pressure for a period of time; and v) reducing the pressure in the container of iv) to ambient pressure and increasing the temperature to 22° C.-37° C. By performing these steps, the cells of v) undergo less apoptosis than a reference.

The reference to which cells treated according to the method of the invention can be compared can be any suitable reference. For example, the reference can be control cells that have not been exposed to one or more of the parameters used to treat the cells using the method of the invention. The reference can be a standardized curve, an area under a curve, a chart, table, or any other presentation of data by which a comparison of the effects of the method of the invention can be made.

In one embodiment, the pressure for holding the cells is between 0.5-4.0 Atm above ambient pressure, and all pressure to the tenth decimal place there between. All pressures mentioned herein unless otherwise indicated mean excess Atm (hyperbaric or super-atmospheric). Ambient pressure means the normal atmospheric pressure without additional pressure, which is typically within the range of 0.84-1.07 Atm, with the average ambient pressure considered to be 1 Atm.

The invention is expected to be suitable for inhibiting apoptosis in any nucleated cell(s). In various embodiments, the cells subjected to the method of the invention are capable of proliferation. The cells may have the potential to differentiate along one or multiple lineages. Thus the cells may have totipotency, pluripotency, multipotency or unipotentcy. The cells may accordingly be stem cells, including but not necessarily limited to adult stem cells, tissue specific stem cells, fetal stem cells, embryonic stem cells, induced pluripotent stem cells, or cancer stem cells. In various embodiments, the cells can be derived from pluripotent cells, such as mesenchymal stem cells or hematopoietic stem cells. For example, myoblasts and cardiomyocytes can be derived from mesenchymal stem cells while hematopoietic stem cells can be derived from bone marrow stem cells. In one embodiment, the cells can be haploid, such as unfertilized oocytes.

In certain embodiments the cells may be immortalized, such as cell lines that are typically established by propagation and/or passaging cells separated from an original source. In other embodiments, the method is used to inhibit apoptosis in cells that have been disaggregated from primary tissue, such as single cell suspensions obtained from a sample of primary tissue. In another embodiment, the cells treated according to the method of the invention may be part of a tissue, including but not limited to a tissue biopsy, a tissue slice, or a tissue culture. In one embodiment, the cells treated using the methods of the invention are free of platelets. In another embodiment, the cells treated using the method of the invention are not present in an organ. The cells may be obtained or derived from any animal. In one embodiment, the animal is a mammal. In one embodiment, the mammal is a human.

As discussed above, the method of the invention involves initially holding nucleated cells in a container and adding xenon (or a gas mixture comprising Xe) to the container so that the pressure inside the container reaches 0.5-4 Atm above ambient pressure, inclusive, and including all digits to the tenth decimal place there between. In this regard, the container can be any container that is suitable to hold a vessel in which the cells are grown and/or stored in vitro. In particular, any vessel, such as a test tube, a flask, Petri dish, Eppendorf tube, tissue culture dish, multi-well culture plate, etc. in which the cells are present can be placed into the container. It will be recognized that when the vessel in which the cells are present is placed in the container, the vessel is configured so that the cells in it are exposed to the added xenon and pressure in the container. For example, if the vessel in which the cells are present is a test tube, the test tube is not sealed, which permits xenon added to the container to exert pressure on and be incorporated into the cells.

The container into which the xenon is added and which holds the vessel in which the cells are present can be any suitable container. Suitable containers may be rigid, such as a jar, a flask, chamber or tube. The container should be capable of maintaining a gas-tight environment. Thus, the container can be capable of being hermetically sealed. The container may also be a flexible, sealable container, an example of which includes but is not limited to a bag. It is preferable for the container and the xenon (or a gas mixture with Xe) that is added to it to be sterile. When performing the method of the invention, any suitable system may be used for adjusting the atmosphere in which the cells are held to provide an atmosphere at a desired partial or total pressure of xenon. The general features of such systems include a reservoir for the gas, whereby the reservoir is preferably operably connected to the container. Suitable gas systems may comprise components including but not limited to valves, pumps, fans, vents, and combinations thereof, as well as a controller for controlling the system components and thereby the amount of gas delivered to the container, and the rate at which the gas is delivered. The system may additionally include one or more components used for evacuation of the xenon comprising atmosphere from the container and/or for creating a vacuum in the container. The entire system or any component or portion of a component may be manually operated, or can be automated so as to be operated by computers and computer programs.

In one embodiment, the cells are stored or exposed to a gas mixture of xenon CO2 and optionally containing nitrogen. Thus, the gas mixture can be from 9% xenon, 5% CO2 and the rest N2 to 95% xenon and 5% CO2. In one embodiment, xenon (or gas mixture comprising xenon) is introduced into the atmosphere within a container, with or without concomitant removal of the existing gas/air, until the concentration of xenon in the gas atmosphere within the container is at least 9%. In one embodiment, the atmosphere in the container consists of xenon. In an alternative embodiment, the atmosphere may consist of xenon and trace impurities. Thus, in one embodiment, the atmosphere may consist essentially of xenon and at least 5% CO2.

The temperature in which the xenon is initially added to the container is variable and will depend on the type of cells that are being treated. In general, the temperature can be between 22° C. and 37° C., inclusive, and including all integers there between, and all numbers between consecutive integers to the tenth decimal point. Irrespective of the temperature during addition of the xenon or a gas mixture containing Xe, once the pressure inside the container reaches 0.5-4 Atm above ambient pressure, the cells are held in the container at the pressure for a period of time during which the temperature in the container is between 22° C. and 37° C., inclusive, and including all digits to the tenth decimal place there between. The period of time during which the cells are held in this temperature and pressure range can vary from 15 minutes to 24 hours, including all intervals of time there between. In connection with this, and while not intending to be constrained by any particular theory, it is considered that holding the cells at 22° C.-37° C. and 0.5-4 Atm above ambient pressure results in the cells becoming saturated with xenon and that this, along with performance of the remaining steps of the method results in inhibition of apoptosis in the cells, which improves the durability of the cells during storage and/or transportation.

After the cells have been held at 0.5 to 4.0 Atm above ambient pressure at 22° C.-37° C. for 15 minutes to 24 hours, the temperature in the container is lowered to between 0.1° C. and 10° C., inclusive, and including all integers there between, and all numbers between consecutive integers to the tenth decimal point, while maintaining the pressure of 0.5 to 4.0 Atm above ambient pressure. In one embodiment, the temperature in the container is lowered by placing the container in a refrigerated enclosure. This range of temperature and pressure is maintained for a period of time, which can range from 2 hours to 3 weeks, including all intervals of time there between, but no less time than is required for the cells inside the container to reach a temperature between 0.1° C. to +10° C. Thus, the invention is useful for storing cells at reduced temperature and increased pressure for 7, 8, 9, 10, 11, 12, 13, 14, or more days.

Subsequent to holding the cells at 0.5 to 4.0 Atm above ambient pressure and 0.1° C. to +10° C., the pressure in the container is reduced to ambient pressure (such as by release of a valve or lid) and the temperature in the container is raised to between to 22° C.-37° C. inclusive, and including all integers there between, and all numbers between consecutive integers to the tenth decimal point. These cells undergo less apoptosis than a reference.

A container containing the cells treated in accordance with the method of the invention may be transported to a location and/or individual or entity for use in a variety of procedures, and the cells will still undergo less apoptosis than a reference.

The invention also provides a refrigerated composition comprising nucleated cells that have been exposed to an elevated concentration of xenon or gas mixture comprising Xe under pressure, but undergo less apoptosis than cells that have not been exposed to the elevated concentration of xenon under pressure.

The following Example is meant to illustrate, but not limit the invention.

In order to obtain the data presented in these Examples, Leukemic monocyte lymphoma cells U-937 were grown in RPMI-1640 medium supplied with 15% fetal bovine serum and 10 mkg/ml gentamicin in the atmosphere of 5% CO2 at 37° C. Petri dishes containing the cell culture in exponential phase of growth were placed into a holding rack and transferred into containers having an inner volume of approximately 1.5 L which were designed for storage in hyperbaric conditions. The mixture of gases Xe—CO2 (95% and 5% respectively) was used for buildup of pressure of 0.5 to 4.0 Atm above ambient pressure over a period of 5-10 minutes, with particular parameters presented in connection with the Figures presented herein. The temperature was held from 22° C. to 37° C. in this embodiment of the invention Gases were mixed in a separate tank (or in the container/tube) based on calculation of their partial pressure. The container with Petri dishes was kept at this temperature and pressure for 2 hrs. Then the container was transferred to a refrigerator with decreased temperature (from 0.1° C. to +5° C.), while maintaining the pressure. The container was held at under these conditions for approximately 4 weeks. After that, the pressure was released and the container holding the cells was kept for 7 days in a household at a temperature of +4° C. to +10° C. and atmospheric pressure.

We chose to treat Jurkat and U-937 cells according to the foregoing procedure because they possess nuclei and full-scale apoptotic cascade mechanisms. Accordingly, these cells respond to a large number of both extracellular and intracellular proapoptotic signals and have been used as model cells for analyzing apoptosis (Pimentel-Muiños F X, Seed B. Regulated commitment of TNF receptor signaling: a molecular switch for death or activation. Immunity. 1999 December; 11 (6):783-93; Karas M, Zaks T Z, Liu J L, LeRoith D. T cell receptor-induced activation and apoptosis in cycling human T cells occur throughout the cell cycle. Mol Biol Cell. 1999 December; 10 (12):4441-50; Valavanis C, Hu Y, Yang Y, Osborne B A, Chouaib S, Greene L, Ashwell J D, Schwartz L M. Model cell lines for the study of apoptosis in vitro. Methods Cell Biol. 2001; 66:417-36).

Figure 1B:
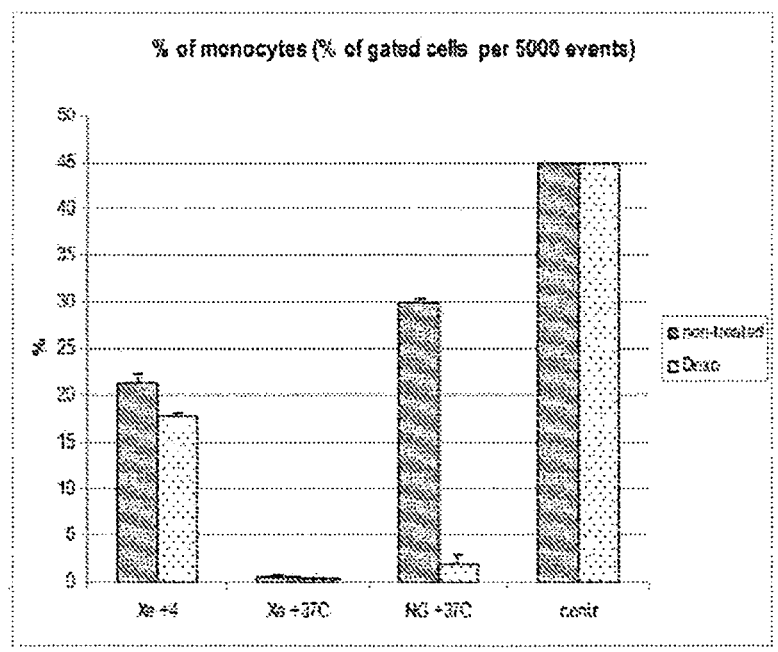
Figure 2:
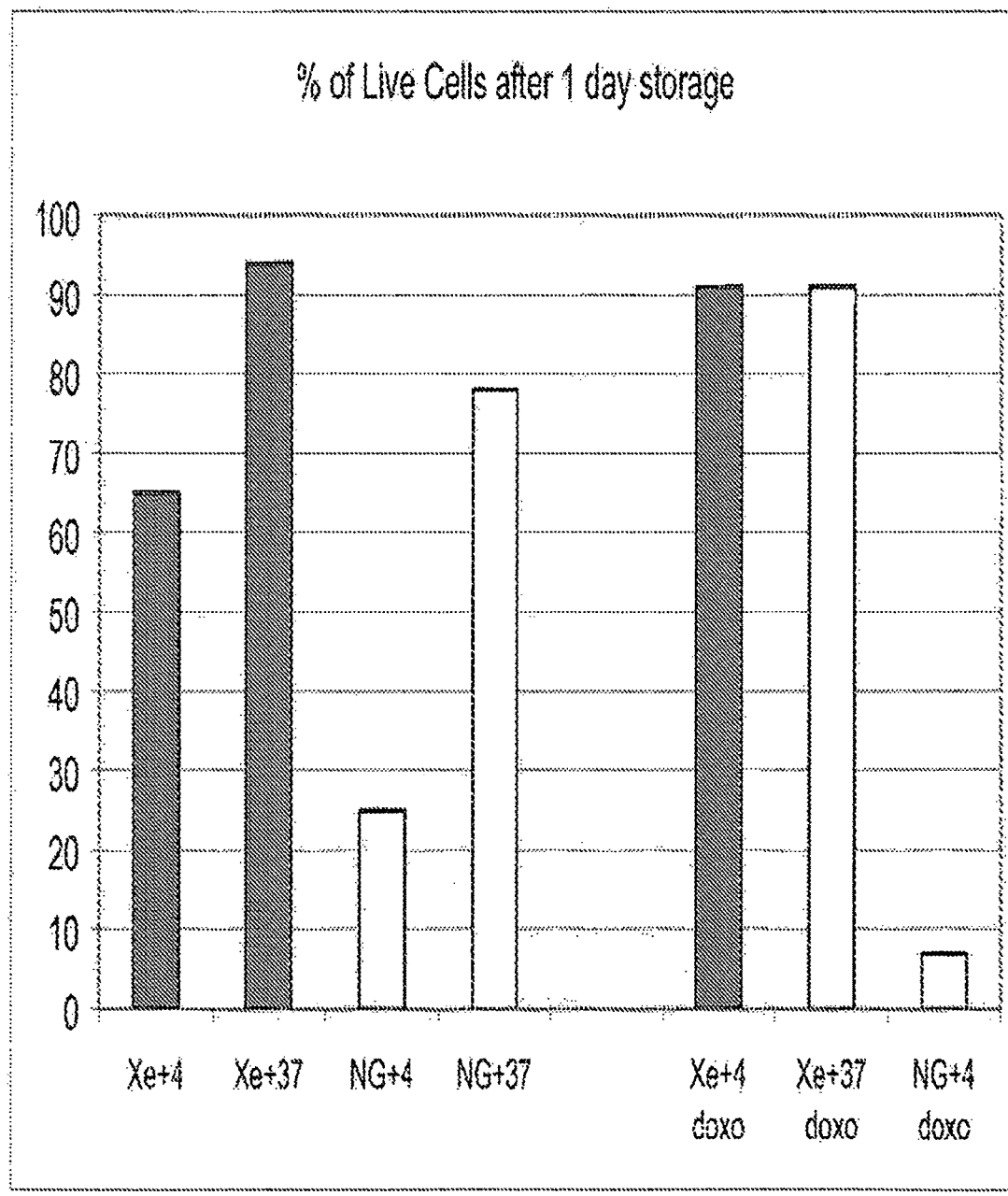
FIG. 2. shows percentage of live leukemic monocyte lymphoma cell line Jurkat cells in relation to total number of cells in 24 hrs of storage at pressure of 4 Atm excessive xenon. Cells were processed as described for FIG. 1. Cells were stored in the presence or absence of an apoptotic inducer doxorubycine (doxo) at the indicated temperatures. Live cells were distinguished from dead cells using a standard trypan blue exclusion assay.

After subjecting the cells to the method of the invention, we analyzed the number of live cells (FIG. 1), and activity of caspase-3 which is indicative of the intensity of apoptosis (FIG. 2). The data presented in FIGS. 1 and 2 establish that the method of the invention inhibits spontaneous death of cells.

Figure 5A:
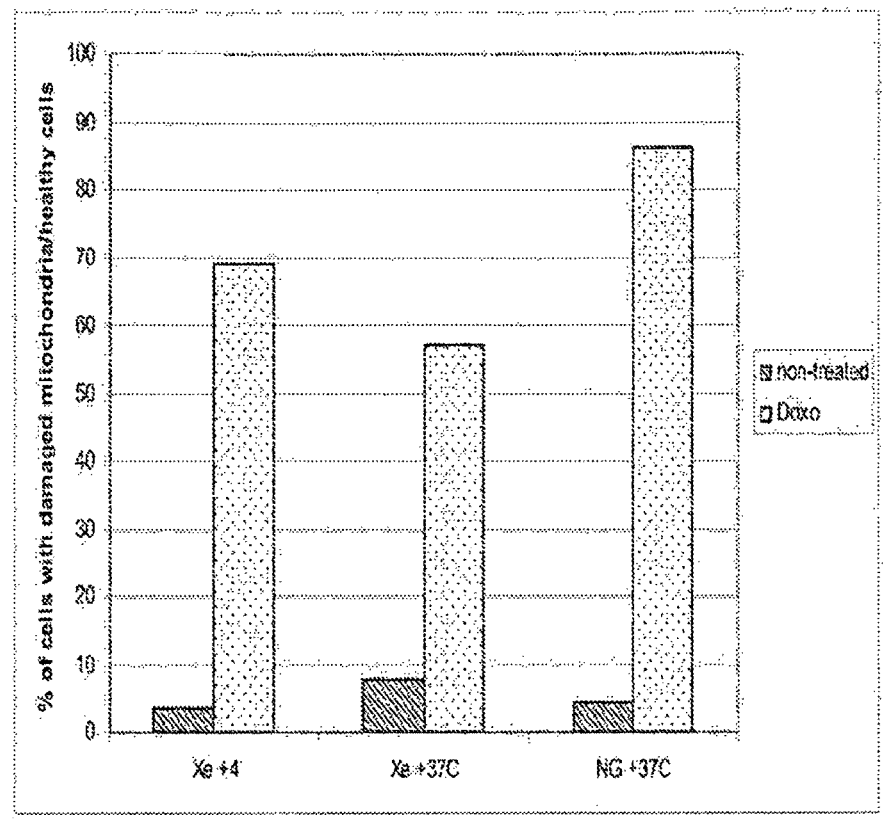
FIG. 5. shows staining of leukemic monocyte lymphoma cell line U-937 cells (stored according to the above-described method during 24 hours (FIG. 5A) and 7 days (FIG. 5B) at pressure of 4 Atm over ambient pressure Xe) with a dyeing agent JC-1 which enables evaluation of the state of mitochondria by flow cytometry.
Figure 5B:
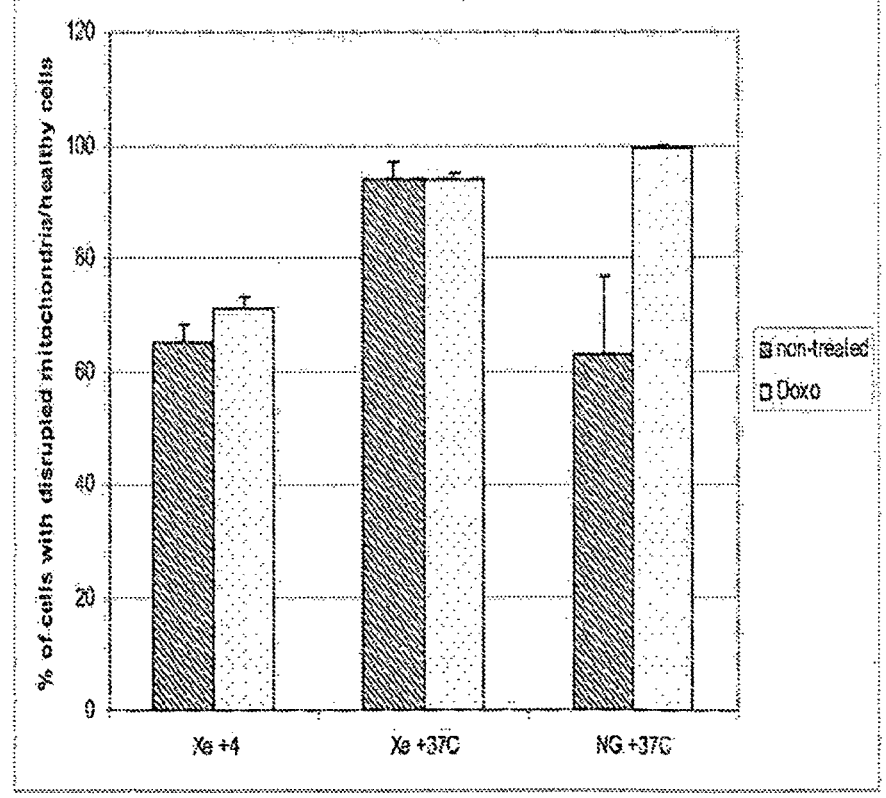
Figure 6:
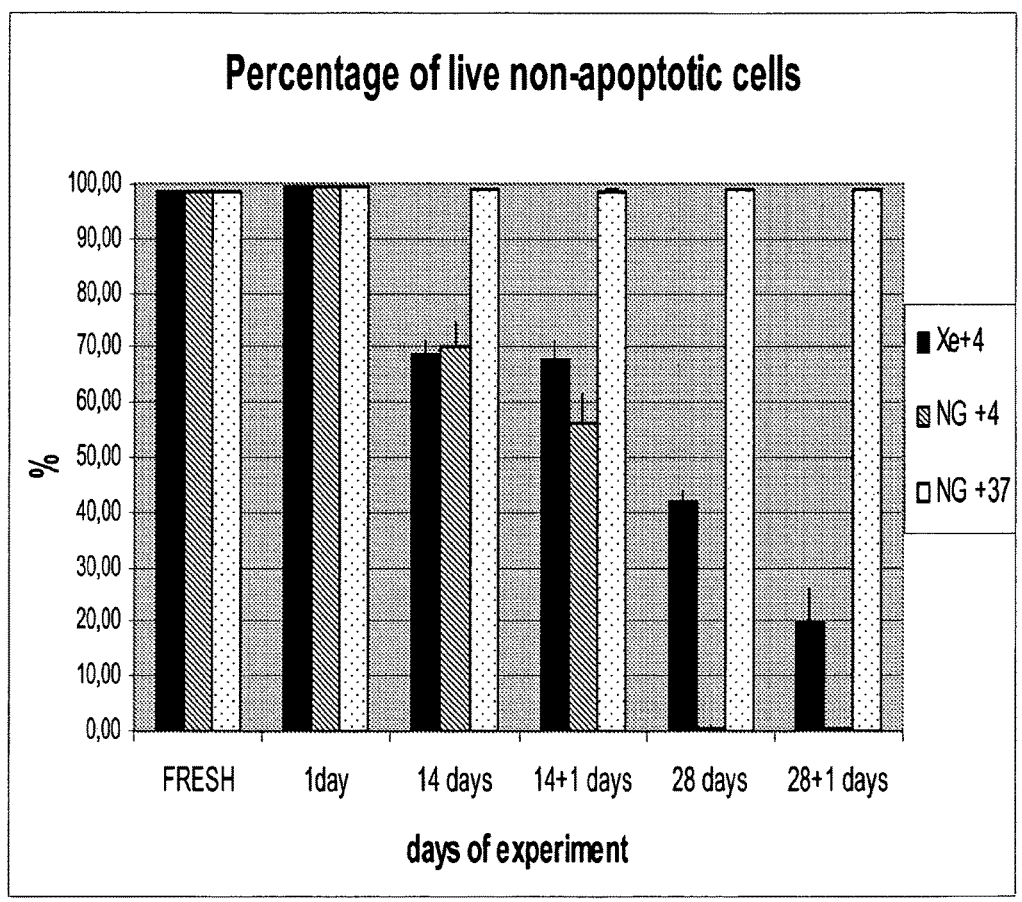
FIG. 6 shows staining of leukemic monocyte lymphoma cell line U-937 cells stored in accordance with the method of the invention at 1, 14 and 28 days of storage. The cells were stained using an Annexin-FITC/Propidium Iodide staining kit which permits differentiating between live, necrotic, early and late apoptotic cells. After the end of storage period, the medium was changed and cells were further cultivated for 1 day in routine conditions to estimate the recovery rate. 'Xe+4': gas mixture 95% Xe+5% CO2 (4 atm excessive pressure) at a +4 C, 'NG+4': storage under ambient pressure and at a temperature of +4 C; NG+37 designated reference samples which cultivated at 37 C, 5% CO2, with replacement of culture medium every three days.

Treatment with xenon also improved cell growth after exposure to doxorubicin (FIG. 3). In particular, reference (control) cells continued to undergo doxorubicin induced death, while an increase in the number of live cells was observed in samples treated with xenon (Xe+37 doxo, Xe+4 doxo). Xenon prevented development of both spontaneous (no Doxo and non-treated) and induced (Doxo) apoptosis in both the Jurkat (FIG. 4) and U-937 cells (FIG. 5

Doxorubicin, being a known apoptosis inducer causes damage to the mitochondrial membrane potential. Xenon (both in combination with cooling and without cooling) exerted protective action on cellular mitochondria. For example, in the presence of xenon, the percentage of doxorubicin-treated cells with undamaged mitochondria was significantly higher than in cells stored without xenon (FIG. 5) both after 24 hrs and 7 days of storage. After 7 days of storage, xenon also significantly decreased damage of mitochondria compared to control (no gas, 37° C.), which is due to the cell growth without cell division in the medium—normally these cells divide every 2-3 days. It is believed that the protection of mitochondria is because the presence of xenon protects the organelles from the action of cold (FIG. 2, groups Xe+4 and NG+4 with and without doxo).

Although the invention has been described in detail for the purposes of illustration, it is understood that such detail is solely for that purpose, and variations can be made therein by those skilled in the art without departing from the spirit and scope of the invention which is defined by the following claims.

We claim:

1. A method for reducing apoptosis in nucleated cells for storage of transportation comprising:
   i) holding nucleated cells in a container, wherein said container is free of platelets;
   ii) adding a gas to said container so that the pressure inside the container reaches 0.5 Atm to 4 Atm above ambient pressure, said gas includes at least 9 vol. % xenon gas;
   iii) maintaining said pressure in said container for a first period of time of up to 24 hours during which a first temperature in said container is 22° C. to 37° C.;
   iv) after said first period of time, lowering said first temperature in the container to a second temperature of 0.1° C.-10° C. while maintaining said pressure at 0.5 Atm to 4 Atm above ambient pressure;
   v) maintaining said container at said second temperature and at a pressure of 0.5 Atm to 4 Atm above ambient pressure for a second period of time, said second period of time different from said first period of time; and,
   vi) after said second period of time, reducing the pressure in said container to 0.84 to 1.07 Atm and increasing said second temperature in said container to up to a third temperature of up to 37° C., said third temperature greater than said second temperature.

2. The method as defined in claim 1, wherein said first period of time is less than said second period of time.

3. The method as defined in claim 1, wherein said first period of time is 15 minutes to 24 hours.

4. The method as defined in claim 3, wherein said second period of time is 2 hours to 2 weeks.

5. The method as defined in claim 1, wherein said second period of time is 2 hours to three weeks.

6. The method as defined in claim 1, wherein said pressure in said container during said second period of time is 3-4 Atm above ambient pressure.

7. The method as defined in claim 1, wherein said second temperature during said second period of time is 4° C.-10° C.

8. The method as defined in claim 1, wherein said pressure is reduced in said container after said second time period over a third period of time, said third period of time is up to 60 minutes.

9. The method as defined in claim 1, wherein said gas consists essentially of xenon gas and carbon dioxide.

10. The method as defined in claim 1, wherein said gas is a gas mixture that includes xenon gas, carbon dioxide gas and nitrogen gas, said xenon gas content is greater than a content of said carbon dioxide gas.

11. The method as defined in claim 1, wherein said gas is a gas mixture that includes xenon gas and carbon dioxide gas, said xenon gas content is greater than a content of said carbon dioxide gas.

12. The method as defined in claim 1, wherein said cells are mammalian cells.

13. The method as defined in claim 1, wherein said cells are human cells.

14. A method for reducing apoptosis in nucleated cells for storage or transportation comprising:
   i) holding nucleated cells in a container, wherein said container is free of platelets;
   ii) adding a gas to said container so that the pressure inside the container reaches 0.5 Atm to 4 Atm above ambient pressure, said gas includes xenon gas and one or more gasses selected from the group consisting of carbon dioxide and nitrogen, said gas includes 9 vol. % to 95 vol. % xenon;
   iii) maintaining said pressure in said container for a first period of time of 15 minutes to 24 hours during which a first temperature in said container is 22° C.-37° C.;
   iv) after said first period of time, lowering said first temperature in the container to a second temperature of 0.1° C.-10° C. while maintaining said pressure in said container at 0.5 Atm to 4 Atm above ambient pressure;
   v) maintaining said container at said second temperature and at a pressure of 0.5 Atm to 4 Atm above ambient pressure for a second period of time of 2 hours to three weeks, said second period of time greater than said first period of time; and,
   vi) after said second period of time, reducing the pressure in said container to 0.84 Atm to 1.07 Atm and increasing said second temperature in said container to up to a third temperature of 22° C. to 37° C. over a period of time that is up to 60 minutes.

15. The method as defined in claim 14, wherein said gas is a gas mixture consisting of xenon gas, carbon dioxide gas and nitrogen gas.

16. The method as defined in claim 14, wherein said xenon gas content is greater than a content of said carbon dioxide gas.

17. The method as defined in claim 14, wherein said gas is a gas mixture that essentially consists of 95 vol. % xenon gas and 5 vol. % carbon dioxide gas.

* * * * *